United States Patent [19]

Garcia

[11] Patent Number: 5,778,475
[45] Date of Patent: Jul. 14, 1998

[54] TONGUE DEBRIDEMENT AID

[76] Inventor: Peter G. Garcia, 1918 East Inglewood, Mesa, Ariz. 85203

[21] Appl. No.: 696,124

[22] Filed: Aug. 13, 1996

[51] Int. Cl.⁶ ............................................. A46B 9/04
[52] U.S. Cl. .......................... 15/111; 15/167.1; 15/176.6
[58] Field of Search ........................... 15/111, 167.1, 15/176.1, 176.6, 235.01, 236.07; 606/160, 161; 128/757, 758

[56] References Cited

U.S. PATENT DOCUMENTS

| | | | |
|---|---|---|---|
| D. 95,777 | 5/1935 | Peterkin et al. | 15/111 |
| 1,741,143 | 12/1929 | Chin | 15/111 |
| 2,049,956 | 8/1936 | Greenberg | 606/161 |
| 2,083,217 | 6/1937 | Brothers et al. | 15/111 |
| 2,651,068 | 9/1953 | Seko | 15/111 |
| 4,488,327 | 12/1984 | Snider | 606/161 |
| 4,683,604 | 8/1987 | Rueb | 15/176.1 |
| 5,282,814 | 2/1994 | Srivastava | 606/161 |
| 5,438,726 | 8/1995 | Leite | 606/161 |

*Primary Examiner*—Terrence Till
*Attorney, Agent, or Firm*—James H. Phillips

[57] ABSTRACT

A tongue debridement aid includes an elongated handle with tongue debridement structure disposed at one end. The tongue debridement structure has a cupped region having an endwall and first and second sidewalls contiguous with the endwall which is disposed at an obtuse angle with respect to said elongated handle and a working edge region disposed along at least the edge of the endwall and typically extends secondarily along the edges of the first and second sidewalls. In use, debris, including microorganisms, may be debrided from the dorsum of the tongue and collected in the cupped region by placing the working edge region on the back of the dorsum, applying moderate pressure and drawing the tongue debridement aid toward the tip of the tongue. The collected debris may then be rinsed away. In order to provide a comprehensive oral hygiene instrument, a fixed or detachable toothbrush head may optionally be provided at the distal end of the elongated handle.

20 Claims, 3 Drawing Sheets

TONGUE DEBRIDEMENT AID

FIELD OF THE INVENTION

This invention relates to the oral hygiene arts and, more particularly, to a tongue debridement aid which may optionally be combined with a permanently detachably affixed toothbrush head.

BACKGROUND OF THE INVENTION

Although it is not well understood among the general public, those skilled in the oral hygiene arts are very well aware that one of the most fertile areas in the mouth for harboring and promoting the reproduction of undesirable microorganisms is the upper surface (dorsum) of the tongue. This fact is of significance not only in furthering an understanding of oral hygiene in general, but because the presence, in large quantities, of such undesirable microorganisms on the dorsum of the tongue is a substantial factor in the generation of halitosis and foul taste. Indeed, this factor may be, and often is, the dominant cause of severe halitosis and, since this fact is not generally well known, a person suffering halitosis typically resorts to the most careful attention to brushing the teeth, the use of mouthwashes and even the ingestion of special purposes capsules which purport to attack the problem of halitosis from within the body. It may therefore be understood why these expedients, more often than not, fail to alleviate halitosis, particularly severe, chronic halitosis. It is to the definitive solution to this problem and to the maintenance of good oral hygiene generally that the present invention is directed.

OBJECTS OF THE INVENTION

It is therefore a broad object of this invention to provide apparatus for safely and effectively removing debris, including microorganisms, from the dorsum of the tongue.

It is another object of this invention to provide such apparatus which is particularly scientifically well adapted to gently, but effectively and safely, mechanically debride the dorsum of the tongue.

In another aspect, it is an object of this invention to provide such apparatus which is simple and may be fabricated at small cost, but which is durable.

In yet another aspect, it is an object of this invention to optionally provide such apparatus in combination with a tooth brush which may be provided with interchangeable toothbrush heads.

SUMMARY OF THE INVENTION

Briefly, these and other objects of the invention are achieved by a tongue debridement aid which includes an elongated handle with tongue debridement structure disposed at one end. The tongue debridement structure has a cupped region having an endwall and first and second sidewalls contiguous with the endwall which is disposed at an obtuse angle with respect to said elongated handle and a working edge region disposed along at least the edge of the endwall and typically extends secondarily along the edges of the first and second sidewalls. In use, debris, including microorganisms, may be debrided from the dorsum of the tongue and collected in the cupped region by placing the working edge region on the back of the dorsum, applying moderate pressure and drawing the tongue debridement aid toward the tip of the tongue. The collected debris may then be rinsed away. This process may be repeated a few times to cover each stretch of the dorsum of the tongue. In order to provide a comprehensive oral hygiene instrument, a fixed or detachable toothbrush head may optionally be provided at the distal end of the elongated handle.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

DESCRIPTION OF THE PREFERRED EMBODIMENTS(S)

Figure 1:
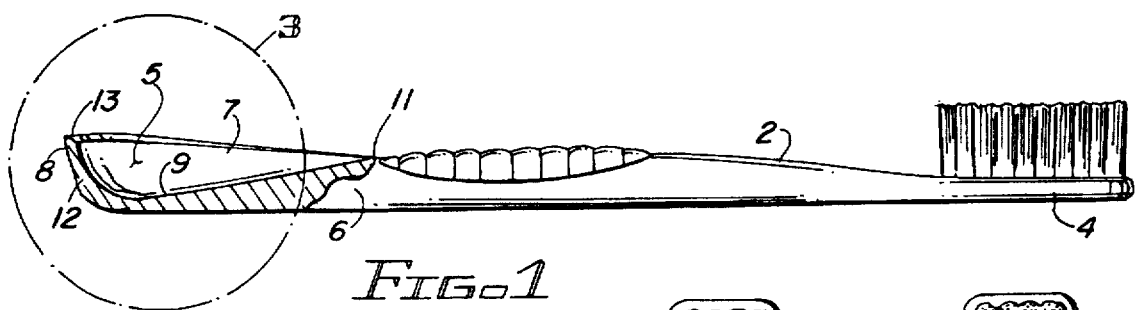
FIG. 1 is a side view of a first embodiment of the invention, partially sectioned to reveal certain inner structure, which incorporates an optional toothbrush head.

Referring first to FIG. 1, a tongue debridement aid in accordance with the present invention is shown in a side view of a first exemplary embodiment which incorporates a toothbrush at a distal end thereof As will be revealed further below, it will be specifically understood that a tongue debridement aid according to the invention may be provided as a single purpose, stand alone device by merely omitting the toothbrush adjunct.

Figure 2:
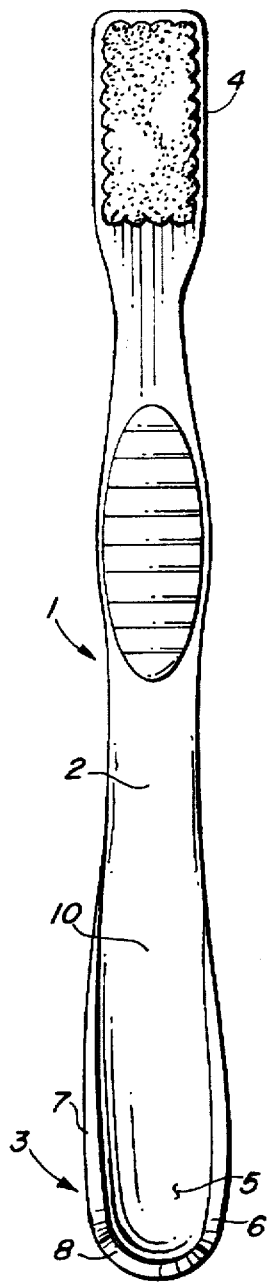
FIG. 2 is a top view of the embodiment of the invention shown in FIG. 1 particularly illustrating a rounded primary working edge.

Referring also to FIG. 2, which is a top view of the first embodiment of the invention, the tongue debridement aid I includes an elongated handle 2 incorporating the tongue debridement structure 3 disposed at one end thereof and a toothbrush head 4 disposed at the distal end.

As best shown in the encircled longitudinally sectioned portion in FIG. 1, the tongue debridement structure 3 includes a hollowed out, cupped region 5 having a continuous wall wrapping three sides. Referring to FIG. 2, it will be seen that sidewall 6 (mostly removed in FIG. 1) is connected to sidewall 7 by rounded endwall 8. The cupped region 5 has a bottom 9 which slopes downwardly from an upper surface 10 of the handle 2 from a region 11 a short distance toward the toothbrush end of the handle and then slopes sharply upwardly in the region 12 to terminate at a working edge region 13.

Figure 3:
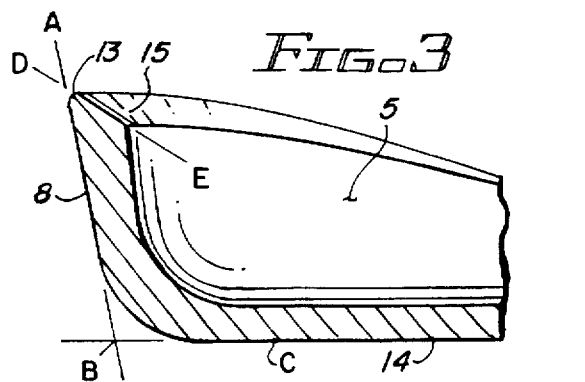
FIG. 3 is an enlarged, sectioned, partial view of the embodiment of the invention shown in FIG. 1 particularly showing certain details of the structure of a working region thereof.

The configuration of the working edge region 13 is important as it serves as the functional interface between the debridement aid and the dorsum of the tongue during use as will be described in more detail below. Thus, referring to the enlarged partial view of FIG. 3, it will first be observed that the rounded endwall 8 is angularly disposed, at its rear apex, in excess of 90° with respect to the bottom edge 14 of the handle 2; i.e., angle ABC >90° and preferably about 95° although this is not a critical angle except that it must be sensibly obtuse for reasons which will become more apparent as the description proceeds.

In addition, the upper edges of the walls 6, 7, 8 are angularly faced off in a bevel as at 15, and, at the rear apex of the endwall 8, the angle of the bevel is about 45°, inwardly sloping, as represented by the angle BDE. It will be especially noted that the working edge region 13, which extends along substantially the extent of the endwall 8 is smoothly rounded, and preferably polished. The corresponding regions of the sidewalls 6, 7 serve as secondary working edges, and the working edge region 13 may, as a practical matter, be considered as including these secondary working edges.

The width of the tongue debridement structure 3, i.e., the maximum outside dimensions between the sidewalls 6, 7 should preferably be at least about one-half inch, and most preferably within the range one-half to threequarters inch, in order to permit debridement of the dorsum of the tongue across substantially its entire surface in three or four overlapping strokes in the manner to be described in more detail below.

Figure 4:
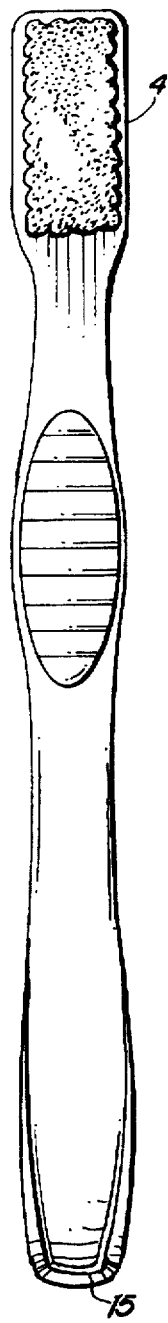
FIG. 4 shows a second embodiment of the invention configured with a modified primary working edge.

FIG. 4 shows a second embodiment of the invention differing from the first embodiment described above only in that, in order to provide a straight primary working edge, the endwall 15 is squared off rather than rounded off as with the endwall 8 as best shown in FIG. 2.

Figure 5:
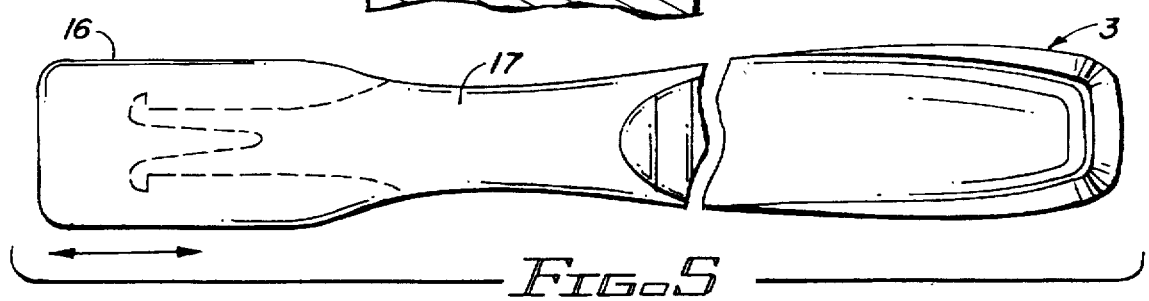
FIG. 5 is a top view of a third embodiment of the invention which incorporates a detachable toothbrush head.

The first and second embodiments of the invention so far described incorporate an optional fixed toothbrush head. Because the debridement aid may be constructed of metal or high quality plastic for durability, an embodiment providing an optional replaceable toothbrush head is also contemplated. Toothbrushes per se incorporating detachable heads are relatively well known in the art. FIG. 5 is a top view of an exemplary third embodiment of the invention which employs a detachable toothbrush head 16 disposed at the distal end of an elongated handle 17 incorporating tongue debridement structure 3 as previously described, and FIGS. 6 and 7 are enlarged, partially broken away, partial views showing the operative structure of the detachable toothbrush head.

Figure 6:
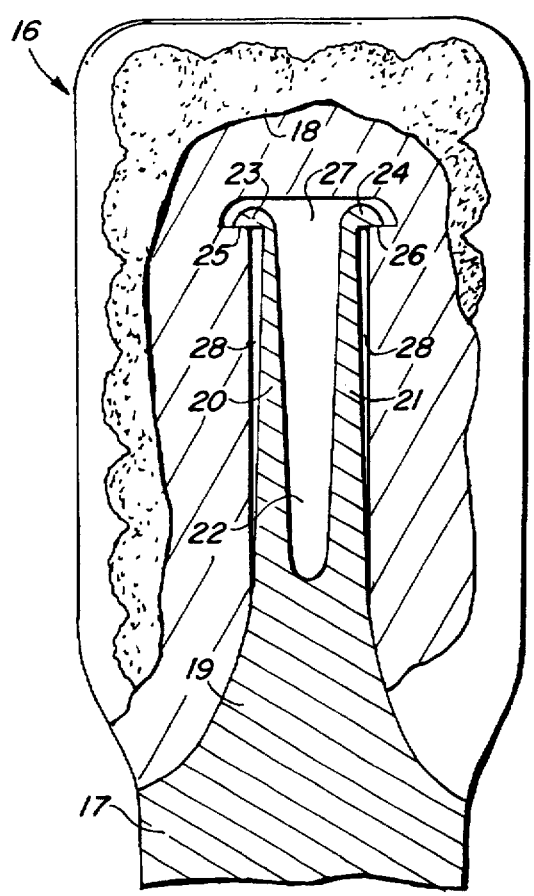
FIG. 6 is an enlarged partial, partially broken away view of the embodiment of the invention shown in FIG. 5 particularly illustrating certain aspects of the internal structure.
Figure 7:
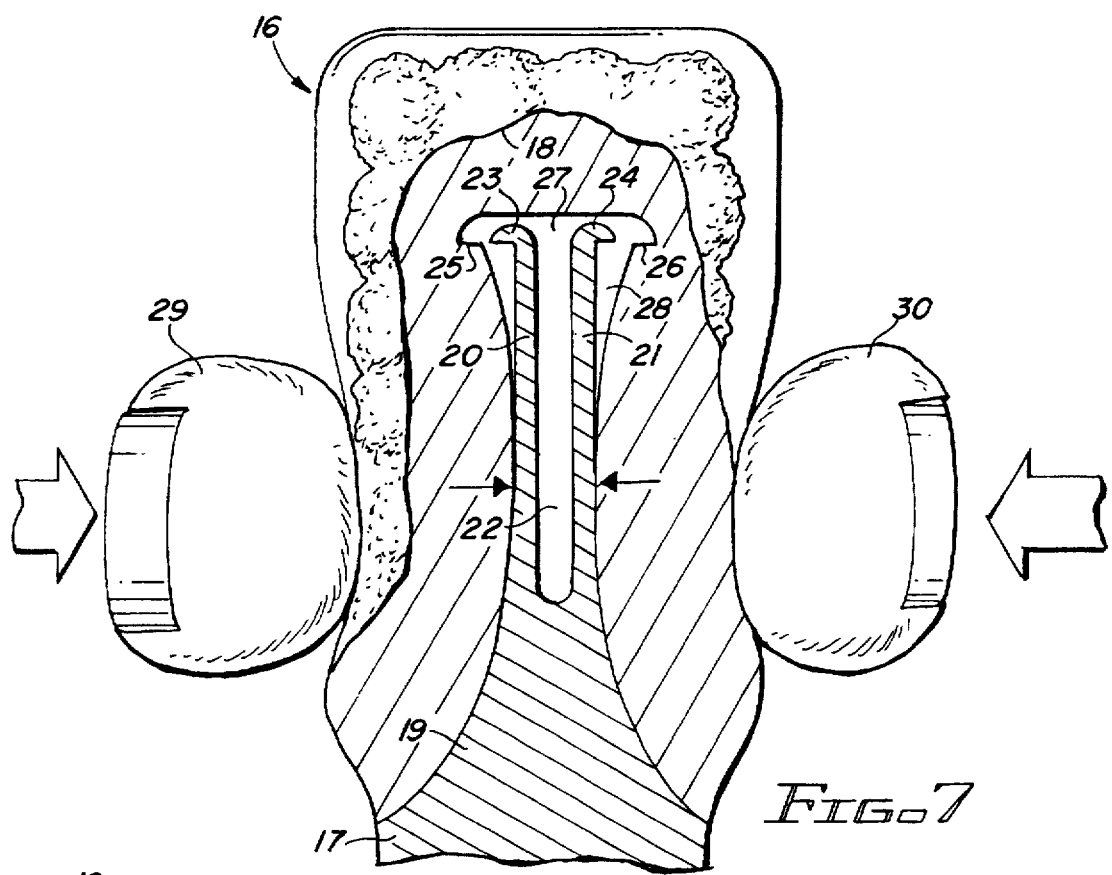
FIG. 7 is a view similar to FIG. 6 illustrating an operation for effecting removal of the detachable toothbrush head.

Referring to FIGS. 6 and 7 in which internal structure for detachably coupling the toothbrush head 16 to the handle 17 is illustrated in the broken away area 18. Integral with and extending from the visible portion of the handle 17 is an inwardly tapered projection 19 which carries first and second detent fingers 20, 21 separated by central slot 22. The material of the handle 17 and the dimensions of the detent fingers 20, 21, are such that the fingers are elastically resilient; i.e., they will readily distort inwardly toward one another as shown in FIG. 7 with appropriate lateral pressure and, will spring back to a relaxed position as shown in FIG. 6 when the lateral pressure is removed.

The detent fingers 20, 21 carry, at their respective outboard ends, catches 23, 24 which normally extend laterally outwardly to respectively selectively engage shoulders 25, 26, provided in a widened portion 27 of a longitudinal chamber 28 formed within the detachable toothbrush head 16. Thus, the view shown in FIG. 6 illustrates the assembly with the toothbrush head 16 rigidly held against and coupled to the handle 17 by the interaction of the catches 23, 24 and the shoulders 25, 26.

FIG. 7 illustrates the assembly at the beginning of an operation to remove the toothbrush head 16, the body of which is itself formed of a resilient material. Thus, inward pressure exerted by a finger 29 and a thumb 30 deflects the engaged portion of the toothbrush head 16 inwardly to accordingly exert inward pressure on each of the detent arms 20, 21. As a result, the catches 23, 24 move inwardly sufficiently to clear the shoulders 25, 26 such that the toothbrush head 16 can easily be withdrawn away from the handle 17. To replace a toothbrush head 16, it is only necessary to start the head over the detent arms 20, 21 such that, as longitudinal force is exerted pushing the head toward the handle 17, the outer tips of the catches 23, 24 ride the inner surface of the longitudinal chamber 28 until the catches snap into position in the widened portion 27 of the chamber to assume the affixed state shown in FIG. 6.

It will be understood that the mechanism shown in FIGS. 6 and 7 for effecting detachability of a toothbrush head to the subject debriding aid is only exemplary and that other mechanisms effectively performing the same operation are contemplated.

Figure 8:
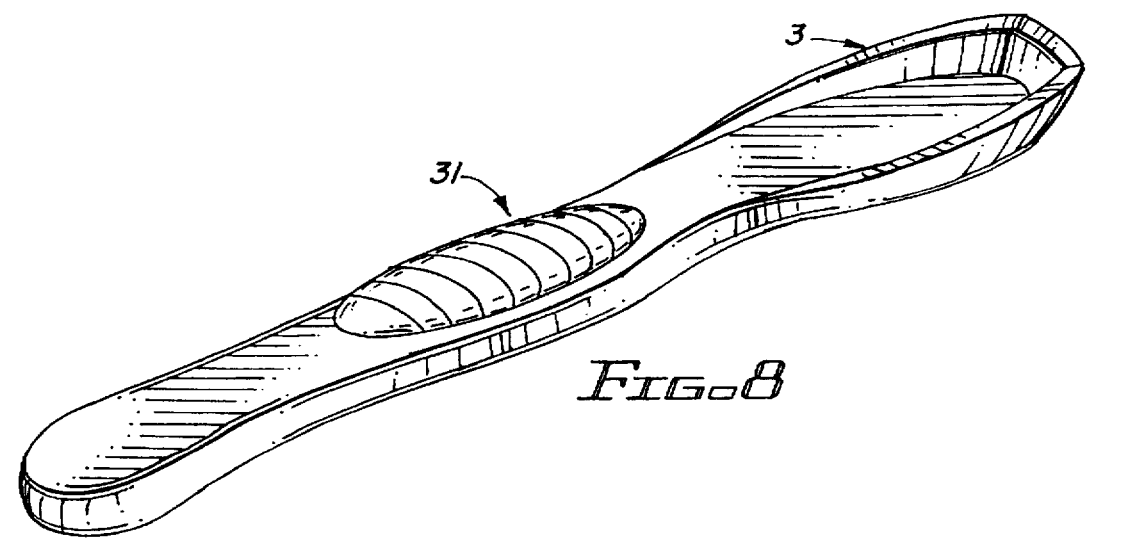
FIG. 8 shows a more basic, fourth embodiment of the invention in which the toothbrush head feature is omitted.

As previously mentioned, a basic embodiment of the invention which omits the toothbrush head feature is independently contemplated, and a single purpose debriding aid 31 incorporating tongue debridement structure 3 is shown in FIG. 8. As with the previously discussed embodiments, the debriding aid 31 may be fabricated from durable plastic or a suitable metal such as stainless steel, either of which must be capable of being sufficiently polished to eliminate sharp, dangerous edges.

Figure 9:
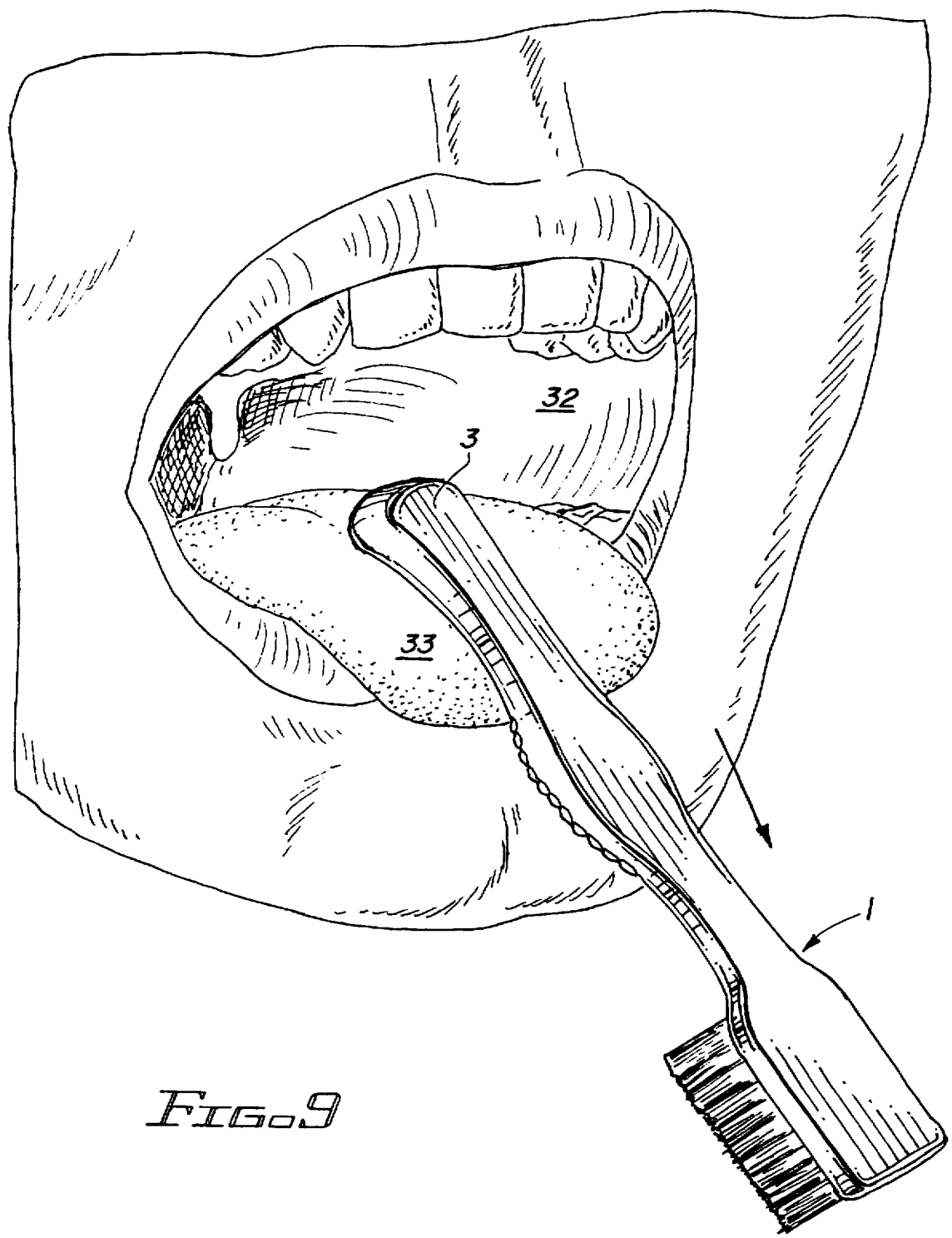
FIG. 9 is a partial pictorial illustrating the preferred manner of using the invention.

FIG. 9 illustrates the use of a debriding aid in accordance with the invention. The open mouth 32 of a user reveals the user's tongue dorsum 33. The debriding operation, preferably carried out at least once a day, conveniently as an adjunct to brushing the teeth, is performed by inserting the debriding aid 1 (the embodiment chosen to illustrate the operation) into the mouth such that the tongue debridement structure 3 rests well back on the tongue dorsum 33 and then pulling the debriding aid forward toward the tip of the tongue while exerting moderate downward pressure. As a result, and referring also to FIGS. 1, 2, 3, the working edge region 13 removes debris, including microorganisms, such that and the debris from the dorsum 33 which is collected in the interior of the cupped region 5 may be for subsequently rinsed away. During this procedure, and as previously noted, it will be understood that the working edge 13 extends along the upper surface of not only the rounded endwall 8 which acts as a primary debrider, but also along the upper surface of the sidewalls 6, 7 which act as secondary debriders gathering debris into the interior of the cupped region 5.

Because of the relatively wide configuration of the tongue debridement structure 3, a few, typically three or four, overlapping strokes serve to effectively debride substantially the entire surface of the tongue dorsum 33 to obtain the benefits of the use of the instrument previously described.

It will now be understood why all sharp edges of the subject tongue debriding aid must be rounded off and, preferably, polished and why the endwall region is preferably disposed at an obtuse angle with respect to the handle. This precaution insures that the tongue debriding aid may be employed in the intended manner without damaging delicate and sensitive tissue within the oral cavity.

Thus, while the principles of the invention have now been made clear in an illustrative embodiment, there will be immediately obvious to those skilled in the art many modifications of structure, arrangements, proportions, the elements, materials, and components, used in the practice of the invention which are particularly adapted for specific environments and operating requirements without departing from those principles.

What is claimed is:

1. A tongue debridement aid comprising:

A) an elongated handle; and

B) tongue debridement structure disposed at one end of said handle, said tongue debridement structure comprising:

1) a cupped region having an endwall and first and second sidewalls contiguous with said endwall; said endwall being disposed at an obtuse angle with respect to said elongated handle; the exterior of the endwall being rounded toward said handle and 2) a working edge region disposed along at least the edge of said endwall, said working edge region being beveled inwardly toward said cupped region;

whereby, debris, including microorganisms, may be debrided from the dorsum of the tongue and collected in said cupped region by placing said working edge region on the back of the dorsum, applying moderate pressure and drawing said tongue debridement aid toward the tip of the tongue.

2. The tongue debridement aid of claim 1 in which said working edge region extends contiguously along the edges of said endwall and said first and second sidewalls.

3. The tongue debridement aid of claim 2 in which said obtuse angle is about 95°.

4. The tongue debridement aid of claim 2 which further includes a toothbrush head disposed at a distal end of said handle.

5. The tongue debridement aid of claim 4 in which said toothbrush head is detachably affixed to said distal end of said elongated handle.

6. The tongue debridement aid of claim 2 in which the beveled angle of said working edge region is about 45°.

7. The tongue debridement aid of claim 6 which further includes a toothbrush head disposed at a distal end of said handle.

8. The tongue debridement aid of claim 7 in which said toothbrush head is detachably affixed to said distal end of said elongated handle.

9. The tongue debridement aid of claim 6 in which said obtuse angle is about 95°.

10. The tongue debridement aid of claim 9 which further includes a toothbrush head disposed at a distal end of said handle.

11. The tongue debridement aid of claim 10 in which said toothbrush head is detachably affixed to said distal end of said elongated handle.

12. The tongue debridement aid of claim 1 in which the beveled angle of said working edge region is about 45°.

13. The tongue debridement aid of claim 12 which further includes a toothbrush head disposed at a distal end of said handle.

14. The tongue debridement aid of claim 13 in which said toothbrush head is detachably affixed to said distal end of said elongated handle.

15. The tongue debridement aid of claim 12 in which said obtuse angle is about 95°.

16. The tongue debridement aid of claim 1 in which said obtuse angle is about 95°.

17. The tongue debridement aid of claim 1 which further includes a toothbrush head disposed at a distal end of said handle.

18. The tongue debridement aid of claim 17 in which said toothbrush head is detachably affixed to said distal end of said elongated handle.

19. The tongue debridement aid of claim 1 in which said working edge is rounded off.

20. The tongue debridement aid of claim 19 in which said working edge has a polished finish.

* * * * *